(12) United States Patent
Poitras et al.

(10) Patent No.: US 11,547,535 B2
(45) Date of Patent: Jan. 10, 2023

(54) SUBPERIOSTEAL DENTAL IMPLANT

(71) Applicant: PANTHERA DENTAL INC., Quebec (CA)

(72) Inventors: Yvan Poitras, St-Aubert (CA); Jean-Pierre Bilodeau, Beaumont (CA)

(73) Assignee: Panthera Dental Inc., Quebec (CA)

( * ) Notice: Subject to any disclaimer, the term of this patent is extended or adjusted under 35 U.S.C. 154(b) by 227 days.

(21) Appl. No.: 16/982,822

(22) PCT Filed: Mar. 14, 2019

(86) PCT No.: PCT/CA2019/050318
§ 371 (c)(1),
(2) Date: Sep. 21, 2020

(87) PCT Pub. No.: WO2019/178673
PCT Pub. Date: Sep. 26, 2019

(65) Prior Publication Data
US 2021/0052355 A1 Feb. 25, 2021

Related U.S. Application Data

(60) Provisional application No. 62/645,906, filed on Mar. 21, 2018.

(51) Int. Cl.
*A61C 8/00* (2006.01)

(52) U.S. Cl.
CPC .......... *A61C 8/0027* (2013.01); *A61C 8/0031* (2013.01)

(58) Field of Classification Search
CPC ... A61C 8/0031; A61C 8/0027; A61C 8/0018; A61C 8/0037; A61C 8/0095; A61B 17/8071; A61B 17/8085; A61B 17/80
See application file for complete search history.

(56) References Cited

U.S. PATENT DOCUMENTS

| 4,741,698 A | * | 5/1988 | Andrews | A61C 8/0075 433/173 |
| 5,002,544 A | * | 3/1991 | Klaue | A61B 17/80 606/280 |

(Continued)

FOREIGN PATENT DOCUMENTS

| GB | 2268409 A | 1/1994 |
| WO | 2009/097386 A1 | 8/2009 |

(Continued)

OTHER PUBLICATIONS

International Preliminary Report on Patentability of PCT/CA2019/050318 dated Sep. 22, 2020, 5 pages.

(Continued)

*Primary Examiner* — Nicholas D Lucchesi
(74) *Attorney, Agent, or Firm* — Brooks Kushman P.C.

(57) ABSTRACT

The present disclosure concerns a subperiosteal dental implant for receiving at least one replacement tooth of a patient, the subperiosteal dental implant comprising an implant frame superposable to at least a section of a jaw bone of the patient, the implant frame having a bone-facing surface at least partially contacting the jaw bone of the patient when the implant frame is superposed thereto, and an opposed gum-facing surface, the implant frame having at least a section along which a cross-section profile includes a base defining at least partially the bone-facing surface and at least partially the gum-facing surface, a ridge protruding from the base and defining at least partially the gum-facing surface, and a first shoulder and a second shoulder that are both defined on the gum-facing surface of the base, each one being located on a respective side of the ridge.

21 Claims, 2 Drawing Sheets

(56) References Cited

U.S. PATENT DOCUMENTS

| | | | | |
|---|---|---|---|---|
| 5,665,089 | A | * | 9/1997 | Dall ................ A61B 17/80 606/908 |
| 6,030,218 | A | * | 2/2000 | Robinson ............. A61C 8/0031 433/173 |
| 6,149,651 | A | * | 11/2000 | Drewry ............... A61F 2/446 606/247 |
| 2005/0192675 | A1 | * | 9/2005 | Robinson ............. A61C 8/0006 623/23.46 |
| 2008/0154310 | A1 | * | 6/2008 | White ............... A61B 17/7059 606/280 |
| 2013/0053976 | A1 | * | 2/2013 | Gugler ................ A61F 2/4637 225/2 |
| 2013/0164707 | A1 | * | 6/2013 | Ali .................. A61K 6/878 433/173 |
| 2016/0000482 | A1 | * | 1/2016 | Ehmke ............... A61B 17/8061 606/71 |
| 2017/0312057 | A1 | | 11/2017 | Cheng |
| 2018/0104028 | A1 | * | 4/2018 | Robichaud ........... A61C 8/0031 |
| 2018/0185098 | A1 | * | 7/2018 | Buck .................. A61F 5/01 |
| 2018/0206895 | A1 | * | 7/2018 | Windolf .............. A61B 17/80 |

FOREIGN PATENT DOCUMENTS

| | | |
|---|---|---|
| WO | 2016/210184 A1 | 12/2016 |
| WO | 2016201580 A1 | 12/2016 |

OTHER PUBLICATIONS

Extended European Search Report from European Patent Application No. EP 3768191, dated Nov. 17, 2021, 9 pages.

\* cited by examiner

SUBPERIOSTEAL DENTAL IMPLANT

CROSS-REFERENCE TO RELATED APPLICATION

This application is the U.S. national phase of international Application No. PCT/CA2019/050318 filed on Mar. 14, 2019 which claims the benefit of U.S. provisional Patent Application No. 62/645,906 filed on Mar. 21, 2018, the disclosures of which are incorporated in their entirety by reference herein.

TECHNICAL FIELD OF THE INVENTION

The present invention relates to the field of dental implant devices. More particularly, the present invention relates to a subperiosteal dental implant.

BACKGROUND

Subperiosteal implants are implants being positioned below a patient's gum and are abutted against, or extend above, the jaw bone, rather than inside the bone. For example and without being limitative, this particular type of implant is commonly used for patients having a shallow jaw bone and which cannot or do not want to undergo a procedure to rebuild the jaw bone.

Subperiosteal implants typically include an implant frame, for instance made of metal, and one or more replacement tooth being attachable to the implant frame. The implant frame is superposable to at least a section of the jaw bone of the patient; it is positioned over the jaw bone and attached thereon, underneath the gum tissue. The one or more replacement tooth is then affixed to the implant frame.

In order to ensure a better fastening of the implant frame of the subperiosteal implant, it is particularly advantageous to make the jaw bone migrate at least partially over the implant frame. This type of implants is known as endosseous implants.

In view of the above, there is a need for a subperiosteal dental implant which would foster the migration of the jaw bone to cover at least partially the implant frame.

BRIEF SUMMARY OF THE INVENTION

It is therefore an aim of the present invention to address the above-mentioned issues.

According to a general aspect, there is provided a subperiosteal dental implant for receiving at least one replacement tooth of a patient, the subperiosteal dental implant comprising an implant frame superposable to at least a section of a jaw bone of the patient, the implant frame having a bone-facing surface at least partially contacting the jaw bone of the patient when the implant frame is superposed thereto, and a gum-facing surface, opposed to the bone-facing surface, the implant frame having at least a section along which a cross-section profile includes a base defining at least partially the bone-facing surface and at least partially the gum-facing surface, a ridge protruding from the base and defining at least partially the gum-facing surface, and a first shoulder and a second shoulder defined on the gum-facing surface of the base, each one being located on a respective side of the ridge.

According to another aspect, there is provided a subperiosteal dental implant for receiving at least one replacement tooth of a patient, the subperiosteal dental implant comprising an implant frame superposable to at least a section of a jaw bone of the patient, the implant frame having a bone-facing surface at least partially contacting the jaw bone when the implant frame is superposed thereto, and a gum-facing surface, the gum-facing surface meeting the bone-facing surface at opposed first and second edges thereof, the gum-facing surface and the bone-facing surface being spaced-apart inbetween the first and second edges, and along at least a section thereof, the implant frame comprising a base defining at least partially the bone-facing surface and at least partially the gum-facing surface, a ridge protruding from the base and defining at least partially the gum-facing surface, the ridge being narrower than the base so as to define a first shoulder and a second shoulder between the ridge and each of the first and second edges.

According to another aspect, the gum-facing surface of the implant frame defines a first base lateral wall segment and a second base lateral wall segment spaced-apart from each other, each one extending from a respective one of the first and second edges, each one of the first and second base lateral wall segments meeting with a respective one of the first and second shoulders through a curved profile.

According to another aspect, the ridge has a curved profile.

According to another aspect, the ridge has a bending radius that is greater than a bending radius of at least one of the curved profiles defined respectively between the first and second base lateral wall segments and the first and second shoulders.

According to another aspect, at least one of the first and second shoulders has a curved profile.

According to another aspect, the bone-facing surface at least partially conforms to an external shape of the jaw bone to which it is superposed.

According to a further general aspect, there is provided a subperiosteal dental implant for receiving at least one replacement tooth of a patient. The subperiosteal dental implant comprises: an implant frame superposable to at least a section of a jaw bone of the patient. The implant frame has: a bone-facing surface at least partially contacting the jaw bone of the patient when the implant frame is superposed thereto, and a gum-facing surface, opposed to the bone-facing surface. The gum-facing surface meets the bone-facing surface at opposed first and second edges thereof. The implant frame has at least a section along which a cross-section profile includes: a base defining at least partially the bone-facing surface and at least partially the gum-facing surface, a ridge protruding from the base and defining at least partially the gum-facing surface, and a first shoulder and a second shoulder defined on the gum-facing surface of the base, each of the first and second shoulders being located on a respective side of the ridge.

According to a still another aspect, there is provided a subperiosteal dental implant for receiving at least one replacement tooth of a patient. The subperiosteal dental implant comprises: an implant frame superposable to at least a section of a jaw bone of the patient. The implant frame has: a bone-facing surface at least partially contacting the jaw bone when the implant frame is superposed thereto, and a gum-facing surface. The gum-facing surface meets the bone-facing surface at opposed first and second edges thereof, the gum-facing surface and the bone-facing surface being spaced-apart in-between the first and second edges, and along at least a section thereof. The implant frame comprises: a base defining at least partially the bone-facing surface and at least partially the gum-facing surface and a ridge protruding from the base and defining at least partially the gum-facing surface, wherein the ridge is narrower than the base so as to define a first shoulder and a second shoulder between the ridge and each of the first and second edges.

In an embodiment, the section of the implant frame extends along a longitudinal direction and wherein considered in a plane substantially perpendicular to the longitudinal direction, a width of the ridge is less than about 90% of a width of the base. Considered in the plane substantially perpendicular to the longitudinal direction, a height of the ridge can be greater than a height of the base.

In an embodiment, the gum-facing surface of the implant frame defines a first base lateral wall segment and a second base lateral wall segment spaced-apart from each other, each one extending transversally from a respective one of the first and second edges up to a respective one of the first and second shoulders. At least a convexity can be defined between the bone-facing surface of the base and at least one of the first and second base lateral wall segments. At least one of the first and second base lateral wall segments can meet with the bone-facing surface of the base through an edge curved profile having an edge bending radius. The first and second base lateral wall segments can meet with the bone-facing surface of the base through first and second edge curved profiles and the edge bending radius of the first and second edge curved profiles are substantially identical. At least one of the first and second base lateral wall segments can meet with a respective one of the first and second shoulders through a lateral curved profile having a lateral bending radius. The first and second base lateral wall segments can meet with the first and second shoulders through first and second lateral curved profiles and the lateral bending radius of the first and second lateral curved profiles can be substantially identical. At least one of the lateral bending radiuses can be greater than at least one of the edge bending radiuses. the at least one of the lateral bending radiuses can be about 2 times greater than the at least one of the edge bending radiuses.

In an embodiment, the ridge has a ridge curved profile. Adjacent to an apex thereof, the ridge can have a ridge bending radius, wherein the gum-facing surface of the implant frame can define a first base lateral wall segment and a second base lateral wall segment spaced-apart from each other, each one extending from a respective one of the first and second edges and meeting with a respective one of the first and second shoulders through first and second lateral curved profiles having a lateral bending radius, the ridge bending radius of the ridge being greater than at least one of the lateral bending radiuses of the first and second lateral curved profiles. The ridge bending radius of the ridge can be at least about 2 times greater than the at least one of the lateral bending radiuses of the first and second lateral curved profiles. At least one of the first and second shoulders can have a shoulder curved profile. The first and second shoulders can have respectively first and second shoulder curved profiles defining a substantially identical shoulder bending radius. The ridge can have a ridge bending radius smaller than a shoulder bending radius of the shoulder curved profile of at least one of the first and second shoulders. The shoulder bending radius can be about 125% of the ridge bending radius of the ridge.

In an embodiment, the bone-facing surface at least partially conforms to an external shape of the jaw bone to which it is superposed.

In an embodiment, the section of the implant frame comprises a first convexity constituted by the ridge. The first convexity can be located at an apex of the section of the implant frame.

In an embodiment, the section of the implant frame further comprises first and second concavities formed at a junction of the first and second shoulders and the ridge.

In an embodiment, the subperiosteal dental implant further comprises at least one implant head extending from the implant frame.

In an embodiment, at least one intersecting strut extends between the first and second edges, the section of the implant frame corresponding to a section of the at least one intersecting strut.

DETAILED DESCRIPTION

Figure 1:
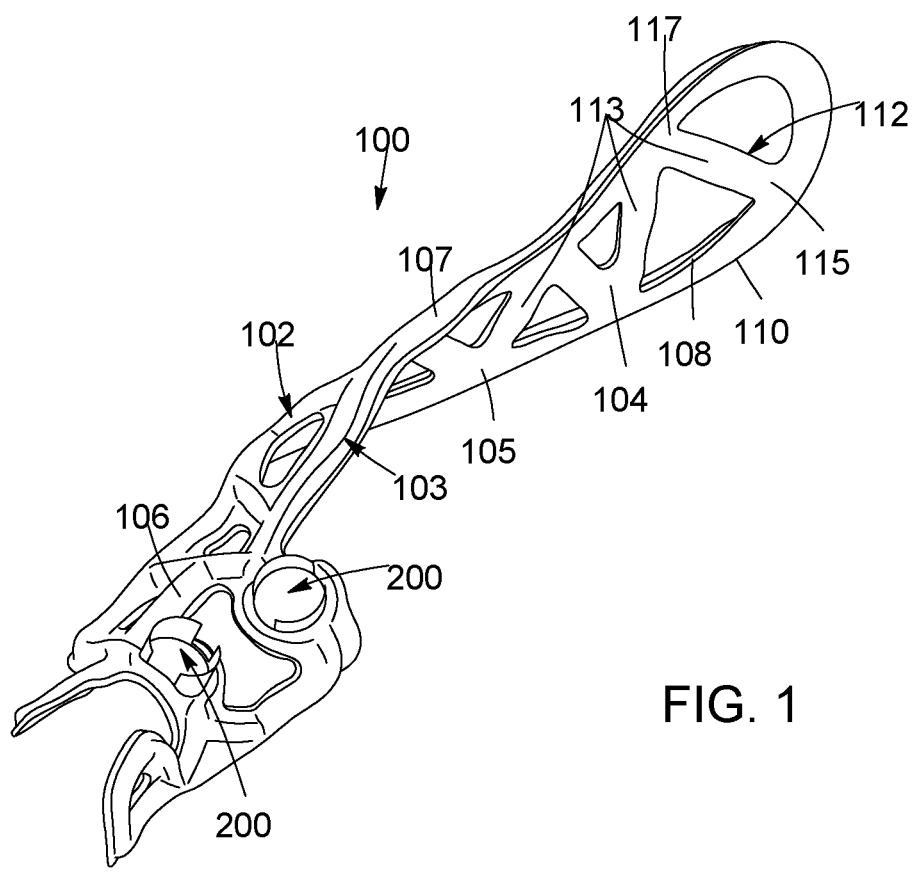
FIG. 1 is a perspective view of a subperiosteal dental implant in accordance with an embodiment.

Moreover, although the embodiments of the subperiosteal dental implant and corresponding parts thereof consist of certain geometrical configurations as explained and illustrated herein, not all of these components and geometries are essential and thus should not be taken in their restrictive sense. It is to be understood, as also apparent to a person skilled in the art, that other suitable components and cooperation therein between, as well as other suitable geometrical configurations, may be used for the subperiosteal dental implant, as will be briefly explained herein and as can be easily inferred herefrom by a person skilled in the art. Moreover, it will be appreciated that positional descriptions such as "above", "below", "left", "right" and the like should, unless otherwise indicated, be taken in the context of the figures and should not be considered limiting.

In the following description, the same numerical references refer to similar elements. Furthermore, for the sake of simplicity and clarity, namely so as to not unduly burden the figures with several references numbers, not all figures contain references to all the components and features, and references to some components and features may be found in only one figure, and components and features of the present disclosure which are illustrated in other figures can be easily inferred therefrom. The embodiments, geometrical configurations, materials mentioned and/or dimensions shown in the figures are optional, and are given for exemplification purposes only.

Moreover, it will be appreciated that positional descriptions such as "above", "below", "forward", "rearward" "left", "right" and the like should, unless otherwise indicated, be taken in the context of the figures and correspond to the position and orientation of the subperiosteal dental implant and corresponding parts when being worn by a patient. Positional descriptions should not be considered limiting.

To provide a more concise description, some of the quantitative expressions given herein may be qualified with the term "about". It is understood that whether the term "about" is used explicitly or not, every quantity given herein is meant to refer to an actual given value, and it is also meant to refer to the approximation to such given value that would reasonably be inferred based on the ordinary skill in the art, including approximations due to the experimental and/or measurement conditions for such given value.

Although various features of the subperiosteal dental implant may be described in the context of a single embodiment, the features may also be provided separately or in any suitable combination. Conversely, although the subperiosteal dental implant may be described herein in the context of separate embodiments for clarity, the subperiosteal dental implant may also be implemented in a single embodiment.

It is to be understood that the phraseology and terminology employed herein is not to be construed as limiting and are for descriptive purpose only.

It is to be understood that the terms "including", "comprising", and grammatical variants thereof do not preclude the addition of one or more components, features, steps, or integers or groups thereof and that the terms are to be construed as specifying components, features, steps or integers.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

The descriptions, examples, methods and materials presented in the claims and the specification are not to be construed as limiting but rather as illustrative only.

Figure 2:
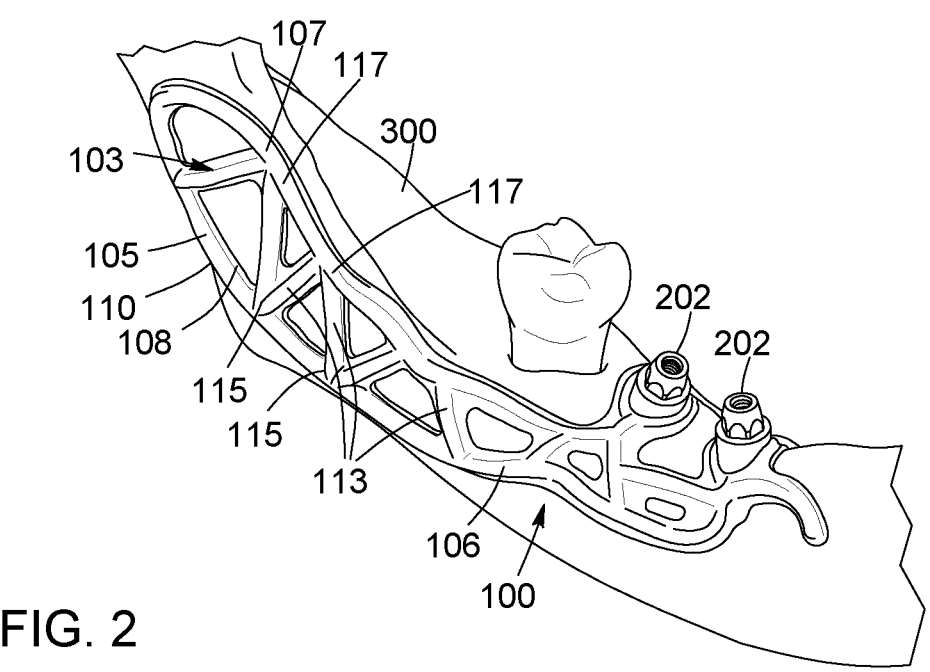
FIG. 2 is a perspective view of the subperiosteal dental implant of FIG. 1, mounted to a section of a jaw bone of a patient.

Referring now to the drawings, and more particularly to FIGS. 1 and 2, there is shown a subperiosteal dental implant 100 that is configured to be mounted to a section 300 of a jaw bone of a patient and that is configured to receive at least one replacement tooth (not represented).

The subperiosteal dental implant 100 includes an implant frame 102 that is configured to be superposed to the section 300 of the jaw bone of the patient. The implant frame 102 is designed to be mounted onto and, more particularly, sit on the external surface of the section 300 of the jaw bone of the patient. For instance and without being limitative, the implant frame 102 can be at least partially made of metal.

In the embodiment shown, the subperiosteal dental implant 100 further comprises one or more implant heads 200 (for instance and without being limitative two, in the embodiment shown) extending from the implant frame 102. The implant heads 200 can be integral (or single piece) with the implant frame 102, i.e. they can be manufactured simultaneously with the implant frame 102 as a single piece. In another embodiment, the implant heads can be fastened or mechanically affixed to the implant frame 102.

Each implant head 200 is configured to engage with one replacement tooth. For instance, each one of the implant heads 200 can have an internally threaded socket adapted to receive a connector 202 to provide an engagement between the replacement tooth and the implant head 200.

As represented in particular in FIGS. 1 and 2, the implant frame 102 of the subperiosteal dental implant 100 according to the present disclosure has a bone-facing surface 104, that is at least partially contacting the section 300 of the jaw bone when the implant frame 102 is superposed to the section 300 of the jaw bone. In a non-limitative embodiment (not shown), the bone-facing surface 104 is dimensioned so as to at least partially conform to an external shape of the section 300 of the jaw bone to which it is superposed. In the embodiment shown, the bone-facing surface 104 is substantially smooth, i.e. protrusion free.

The implant frame 102 further comprises a gum-facing surface 106 that is opposed to the bone-facing surface 104.

The gum-facing surface 106 meets the bone-facing surface 104 at opposed first and second edges 108, 110 of the bone-facing surface 104. Between the first and second edges 108, 110, the gum-facing surface 106 and the bone-facing surface 104 are spaced-apart one from the other. In the shown embodiment, the first and second edges 108, 110 have a rounded profile.

In the embodiments shown in FIGS. 1 and 2, the implant frame 102 comprises a substantially longitudinal body 103 comprising first and second longitudinal members 105, 107, extending substantially longitudinally and spaced-apart from one another and a plurality of intersecting struts 113 extending between the first and second longitudinal members 105, 107. Each of the struts 113 comprises a first end portion 115 engaged to the first longitudinal member 105, and a second end portion 117 engaged to the second longitudinal member 107. For instance and without being limitative, some adjacent struts 113 have their first end portions 115 adjacent each other while their second end portions 117 are spaced apart from each other; some other adjacent struts 113 have their second end portions 117 adjacent each other while their first end portions 115 are spaced apart from each other. In other words, some adjacent struts 113 might form a substantially V-shape strut assembly extending between the first and second longitudinal members 105, 107 of the longitudinal body 103 of the implant frame 102.

It is appreciated that the shape and the configuration of the implant frame, as well as the shape, the number, the configuration and the respective arrangement of the first and second longitudinal members and the struts extending therebetween can vary from the embodiment shown.

Figure 3:
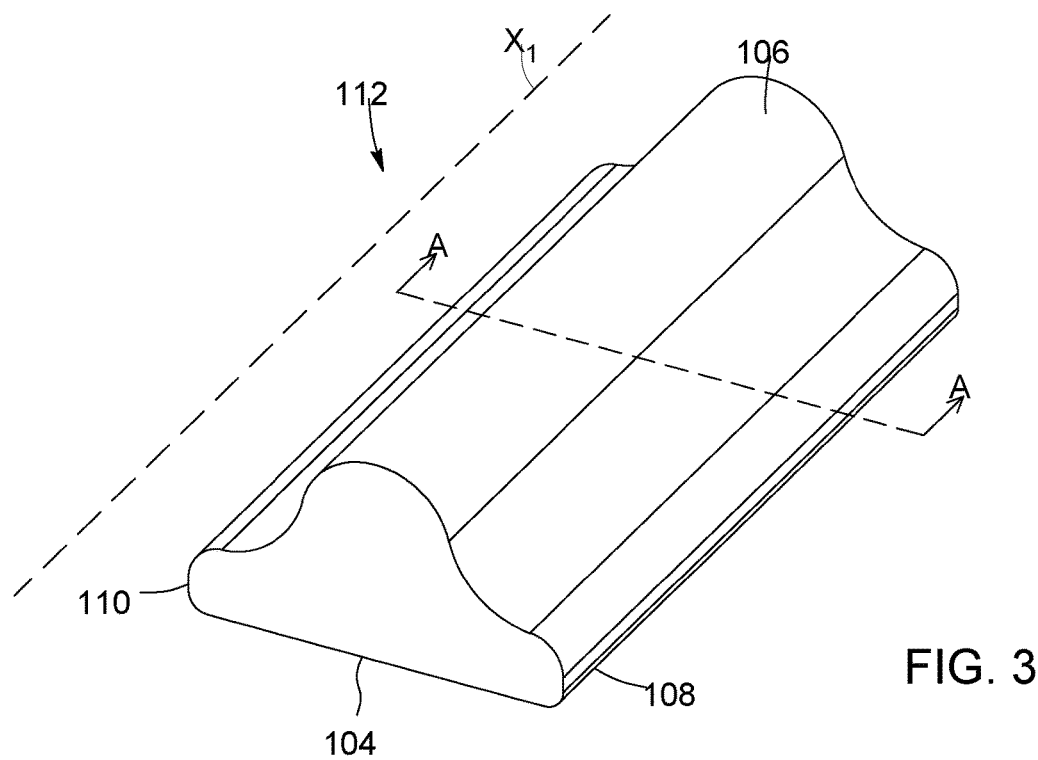
FIG. 3 is a perspective view of a section of an implant frame of a subperiosteal dental implant according to an embodiment of the present disclosure.
Figure 4:
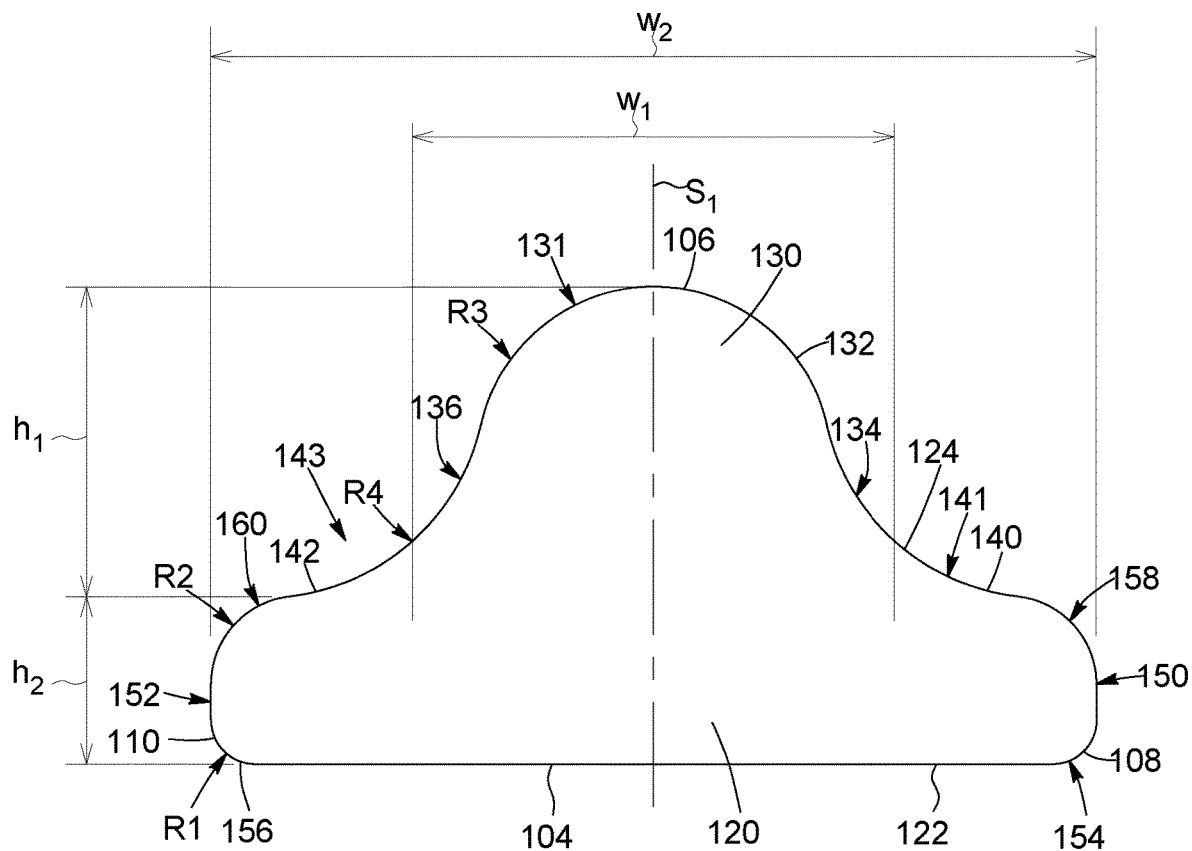
FIG. 4 is a sectional view taken along cross-section lines A-A of the section of the implant frame represented on FIG. 3.

As it appears in particular in FIGS. 3 and 4 that represent a section 112 of the implant frame 102, and more particularly a section 112 of one of the intersecting struts 113. It is appreciated that the section could be taken or could represent one of the first and second longitudinal members 105, 107 of the longitudinal body 103. The section 112 has a cross-section profile defined by the gum-facing surface 106 and the bone-facing surface 104. The section 112 of the strut 113 extends along a longitudinal direction X1. Along at least the section 112 of the intersecting strut 113 of the implant frame 102, it comprises a base 120 and a ridge 130 that protrudes from the base 120. It is appreciated that, in other sections, the longitudinal body 103 of the implant frame 102 can include solely the base 120 and be free or substantially free of ridge 130.

The base 120 has a first face 122 that partially defines the bone-facing surface 104, and an opposed second face 124, that partially defines the gum-facing surface 106. The first and second faces 122, 124 are mostly spaced-apart from the other and meets at the first and second edges 108, 110.

Along at least the section 112 of the intersecting strut 113 of the implant frame 102, the ridge 130 has an outer face 132 that partially defines the gum-facing surface 106. The outer face 132 of the ridge 130 merges with the second face 124 of the base at a virtual junction between the base 120 and the ridge 130.

The ridge 130 is narrower than the base 120 and extends substantially centrally from the base 120. Considered in a plane substantially perpendicular to the longitudinal direction X1, as represented in FIG. 4, a width w1 of the ridge 130 is less than about 90% of a width w2 of the base 120. In another embodiment, the width w1 of the ridge 130 is less than about 80% of the width w2 of the base 120. In another embodiment, the width w1 of the ridge 130 is less than about 70% of the width w2 of the base 120. In yet another embodiment, the width w1 of the ridge 130 is less than about 60% of the width w2 of the base 120. Considered in a plane substantially perpendicular to the longitudinal direction X1, as represented in FIG. 4, the ridge 130 has a height h1 that is at least equal to a height h2 of the base 120. In an embodiment, the height h1 of the ridge 130 is greater than the height h2 of the base 120. In another embodiment, the height h1 of the ridge 130 is at least about 110% of the height h2 of the base 120. In another embodiment, the height h1 of the ridge 130 is at least about 120% of the height h2 of the base 120. In yet another embodiment, the height h1 of the ridge 130 is at least about 130% of the height h2 of the base 120.

In other words, in the portions where the first and second faces 122, 124 are spaced-apart from one another, the first and second faces 122, 124 are separated from each other from a distance smaller than or equal to the height h2 of the base 120.

In an embodiment, the width w2 of the base 120 is between about 1 mm and about 4 mm. In another embodiment, the width w2 of the base 120 is between about 2 mm and about 3 mm. In another embodiment, the width w2 of the base 120 is about 2.5 mm.

In an embodiment, the width w1 of the ridge 130 is between about 0.5 mm and about 3 mm. In another embodiment, the width w1 of the ridge 130 is between about 1 mm and about 2.5 mm. In another embodiment, the width w1 of the ridge 130 is about 1.5 mm.

In an embodiment, the height h1 of the ridge 130 is between about 0.5 mm and about 2 mm. In another embodiment, the height h1 of the ridge 130 is between about 0.75 mm and about 1.5 mm. In another embodiment, the height h1 of the ridge 130 is about 1 mm.

In an embodiment, the height h2 of the base 120 is between about 0.1 mm and about 0.7 mm. In another embodiment, the height h2 of the base 120 is between about 0.2 mm and about 0.6 mm. In another embodiment, the height h2 of the base 120 is about 0.4 mm.

In the embodiment shown, the width w2 of the base 120 is greater than the height h2 of the base 120. In an embodiment, the width w2 of the base 120 is at least about 2 times greater than the height h2 of the base 120. In another embodiment, the width w2 of the base 120 is at least about 3 times greater than the height h2 of the base 120. In yet another embodiment, the width w2 of the base 120 is at least about 4 times greater than the height h2 of the base 120.

In the embodiment shown, the width w1 of the ridge 130 is substantially equal to the height h1 of the ridge 130.

In other words, the cross-section profile of the section 112 of the implant frame 102 is substantially T-shaped (inverted, with regards to the relative arrangement of the bone-facing surface 104 and the gum-facing surface 106).

It is thus understood that, along the section 112 of the implant frame 102, the cross-section profile defined by the gum-facing surface 106 defines a first shoulder 140 and a second shoulder 142. The first shoulder 140 is defined from a first side 134 of the ridge 130 towards the first edge 108 of the bone-facing surface 104, whereas the second shoulder 142 is defined from a second side 136 of the ridge 130 towards the second edge 110 of the bone-facing surface 104.

It is thus understood that the first shoulder 140 and the second shoulder 142 are defined on the gum-facing surface 106 of the base 120, each of the first and second shoulders 140, 142 being located on the corresponding side 134, 136 of the ridge 130.

As represented in particular on FIG. 4, the gum-facing surface 106 comprises, at least along the section 112 of the implant frame 102 of the subperiosteal dental implant 100, a first base lateral wall segment 150 that extends transversally, in an embodiment substantially perpendicularly, from the first edge 108.

The gum-facing surface 106 further comprises, at least along the section 112 of the implant frame 102, a second base lateral wall segment 152 that extends transversally, in an embodiment substantially perpendicularly, from the second edge 110. The first and second base lateral wall segments 150, 152 extend thus substantially parallelly spaced-apart from each other.

It is thus understood that the first shoulder 140 is defined between the first side 134 of the ridge 130 and the first base lateral wall segment 150, whereas the second shoulder 142 is defined between the second side 136 of the ridge 130 and the second base lateral wall segment 152.

The first and second base lateral wall segments 150, 152 both meet the bone-facing face 104 of the base 120 through first and second edge curved profiles 154, 156 substantially corresponding to the first and second edges 108, 110.

In the embodiment shown, the first and second edge curved profiles 154, 156 defined respectively at a junction of the first and second base lateral wall segments 150, 152 and the bone-facing surface 104 of the base 120, i.e. the first and second edges 108, 110, are identical and have an edge bending radius R1.

In an embodiment, the edge bending radius R1 is comprised between about 0.05 mm and about 0.2 mm. In another embodiment, the edge bending radius R1 is comprised between about 0.1 mm and about 0.15 mm. In another embodiment, the edge bending radius R1 is about 0.125 mm.

The first and second base lateral wall segments 150, 152 also meet respectively with the first and second shoulders 140, 142 through first and second lateral curved profiles 158, 160.

It is understood that the first and second lateral curved profiles 158, 160 are respectively defined between the first and second base lateral wall segments 150, 152 and the gum-facing surface 106 defined by the base 120.

In the embodiment shown, the first and second lateral curved profiles 158, 160 defined respectively between the first and second base lateral wall segments 150, 152 and the first and second shoulders 140, 142 are identical and have a lateral bending radius R2.

In an embodiment, the lateral bending radius R2 is comprised between about 0.1 mm and about 0.4 mm. In another embodiment, the lateral bending radius R2 is comprised between about 0.2 mm and about 0.3 mm. In another embodiment, the lateral bending radius R2 is about 0.25 mm.

In the embodiment shown, the lateral bending radius R2 is greater than the edge bending radius R1. In an embodiment, the lateral bending radius R2 is at least about 110% of the edge bending radius R1. In another embodiment, the lateral bending radius R2 is at least about 150% of the edge bending radius R1. In another embodiment, the lateral bending radius R2 is at least about 170% of the edge bending radius R1. In yet another embodiment, the lateral bending radius R2 is at least about 2 times greater than the edge bending radius R1.

At an apex thereof, the ridge 130 also has a ridge curved profile 131 and defines a ridge bending radius R3.

In an embodiment, the ridge bending radius R3 is comprised between about 0.2 mm and about 0.8 mm. In another embodiment, the ridge bending radius R3 is comprised between about 0.4 mm and about 0.6 mm. In another embodiment, the ridge bending radius R3 is about 0.5 mm.

For instance, the ridge bending radius R3 of the ridge curved profile 131 of the ridge 130 is greater than the lateral bending radius R2. In an embodiment, the ridge bending radius R3 is at least about 110% of the lateral bending radius R2. In another embodiment, the ridge bending radius R3 is at least about 150% of the lateral bending radius R2. In another embodiment, the ridge bending radius R3 is at least about 170% of the lateral bending radius R2. In yet another embodiment, the ridge bending radius R3 is at least about 2 times greater than the lateral bending radius R2.

The first and second shoulders 140, 142 also have first and second shoulder curved profiles 141, 143, at their respective junction with the ridge 130. In the embodiment shown, the first and second shoulder curved profiles 141, 143 of the firsts and second shoulders 140, 142 are identical and define a shoulder bending radius R4.

In an embodiment, the shoulder bending radius R4 is comprised between about 0.4 mm and about 0.8 mm. In another embodiment, the shoulder bending radius R4 is comprised between about 0.55 mm and about 0.7 mm. In another embodiment, the shoulder bending radius R4 is about 0.625 mm.

In the embodiment shown, the shoulder bending radius R4 is greater than the ridge bending radius R3. In an embodiment, the shoulder bending radius R4 is at least about 105% of the ridge bending radius R3. In another embodiment, the shoulder bending radius R4 is at least about 115% of the ridge bending radius R3. In yet another embodiment, the shoulder bending radius R4 is at least about 125% of the ridge bending radius R3.

As it appears in particular on FIG. 4, at least along the section 112 of the intersecting strut 113 of the implant frame 102, the cross-section profile comprises, on the gum-facing surface 106, a first convexity constituted by the ridge 130 and the ridge bending radius R3, the first convexity being located at an apex of the implant frame 102, between two additional convexities constituted by the first and second lateral curved profiles 158, 160 that are defined respectively between the first and second base lateral wall segments 150, 152 and the corresponding first and second shoulders 140, 142.

It is further understood that the cross-section profile comprises, on the gum-facing surface 106, at least along the section 112 of the implant frame 102, first and second concavities that are constituted respectively by the first and second shoulder curved profiles 141, 143 located at a junction of the first and second shoulders 140, 142 and the ridge 130, on a respective side thereof.

It is also understood that at each of the first and second edges 108, 110 of the bone-facing surface 104, convexities are also defined by the first and second edge curved profiles 154, 156 defined between the bone-facing surface 104 of the base 120 and the first and second base lateral wall segments 150, 152.

In other words, at least along the section 112 of the implant frame 102, the cross-section profile defined by the gum-facing surface 106 and the bone-facing surface 104 only defines curved profiles, such a configuration being particularly favorable for the migration of the jaw bone at least partially over the subperiosteal dental implant 100. The implant frame 102 according to the present disclosure is thus particularly efficient for the jaw bone to increase and migrate towards the gum of the patient so as to at least partially cover the gum-facing surface 106 of the implant frame 102.

As represented in particular on FIG. 4, the cross-section profile defined by the gum-facing surface 106 and the bone-facing surface 104 at least along the section 112 of the implant frame 102 has an axis of symmetry S1 that extends transversally, at a median thereof, which can correspond to the apex of the ridge 130, to the bone-facing surface 104 of the base 120. It is nonetheless appreciated that, in alternative embodiments (not shown), the cross-section profile defined by the gum-facing surface 106 and the bone-facing surface 104 could be asymmetrical.

It is appreciated that the shape, the configuration, the location and the relative arrangement of the ridge and the first and second shoulders can vary from the embodiment shown.

It is appreciated that one or several of the intersecting struts 113 of the implant frame 102 can include the above-described profile along their length or along a section thereof. Therefore, the section 112 can be along an entire length of an intersecting strut 113 or along only a section of their length. Furthermore, in an embodiment, almost all or all the intersecting struts 113 of the implant frame 102 can include the above-described profile at least along a section of their length. It is further understood that an implant frame 102 having intersecting struts 113 with different profiles could be conceived. Moreover, it could also be conceived an implant frame 102 having any other shape, or having at least one of the first and second longitudinal members 105, 107 with a portion comprising a profile according to the present disclosure.

The embodiments of the invention described above are intended to be exemplary only. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind. The scope of the invention is therefore intended to be limited solely by the scope of the appended claims.

The invention claimed is:

1. A subperiosteal dental implant for receiving at least one replacement tooth of a patient, the subperiosteal dental implant comprising:
   an implant frame superposable to at least a section of a jaw bone of the patient, the implant frame having:
      a bone-facing surface at least partially contacting the jaw bone of the patient when the implant frame is superposed thereto, and
      a gum-facing surface, opposed to the bone-facing surface,
      the gum-facing surface meeting the bone-facing surface at opposed first and second edges thereof;
   the implant frame having at least a section along which a cross-section profile includes:
      a base defining at least partially the bone-facing surface and at least partially the gum-facing surface,
      a ridge protruding from the base and defining at least partially the gum-facing surface, and a first shoulder and a second shoulder defined on the gum-facing surface of the base, each of the first and second shoulders being located on a respective side of the ridge.

2. The subperiosteal dental implant according to claim 1, wherein the section of the implant frame extends along a longitudinal direction and wherein considered in a plane substantially perpendicular to the longitudinal direction, a width of the ridge is less than about 90% of a width of the base.

3. The subperiosteal dental implant according to claim 2, wherein, considered in the plane substantially perpendicular to the longitudinal direction, a height of the ridge is greater than a height of the base.

4. The subperiosteal dental implant according to claim 1, wherein the gum-facing surface of the implant frame defines a first base lateral wall segment and a second base lateral wall segment spaced-apart from each other, each one extending transversally from a respective one of the first and second edges up to a respective one of the first and second shoulders.

5. The subperiosteal dental implant according to claim 4, wherein at least a convexity is defined between the bone-facing surface of the base and at least one of the first and second base lateral wall segments.

6. The subperiosteal dental implant according to claim 4, wherein at least one of the first and second base lateral wall segments meets with the bone-facing surface of the base through an edge curved profile having an edge bending radius.

7. The subperiosteal dental implant according to claim 6, wherein the first and second base lateral wall segments meet with the bone-facing surface of the base through first and second edge curved profiles and the edge bending radius of the first and second edge curved profiles are substantially identical.

8. The subperiosteal dental implant according to claim 6, wherein at least one of the first and second base lateral wall segments meets with a respective one of the first and second shoulders through a lateral curved profile having a lateral bending radius.

9. The subperiosteal dental implant according to claim 8, wherein the first and second base lateral wall segments meet with the first and second shoulders through first and second lateral curved profiles and the lateral bending radius of the first and second lateral curved profiles are substantially identical.

10. The subperiosteal dental implant according to claim 8, wherein at least one of the lateral bending radiuses is greater than at least one of the edge bending radiuses.

11. The subperiosteal dental implant according to claim 1, wherein the ridge has a ridge curved profile and wherein, adjacent to an apex thereof, the ridge has a ridge bending radius, wherein the gum-facing surface of the implant frame defines a first base lateral wall segment and a second base lateral wall segment spaced-apart from each other, each one extending from a respective one of the first and second edges and meeting with a respective one of the first and second shoulders through first and second lateral curved profiles having a lateral bending radius, the ridge bending radius of the ridge being greater than at least one of the lateral bending radiuses of the first and second lateral curved profiles.

12. The subperiosteal dental implant according to claim 11, wherein at least one of the first and second shoulders has a shoulder curved profile.

13. The subperiosteal dental implant according to claim 12, wherein the first and second shoulders have respectively first and second shoulder curved profiles defining a substantially identical shoulder bending radius.

14. The subperiosteal dental implant according to claim 12, wherein the ridge has a ridge bending radius smaller than a shoulder bending radius of the shoulder curved profile of at least one of the first and second shoulders.

15. The subperiosteal dental implant according to claim 1, wherein the bone-facing surface is configured to at least partially conform to an external shape of the jaw bone to which it is superposed.

16. The subperiosteal dental implant according to claim 1, wherein the section of the implant frame comprises a first convexity constituted by the ridge and wherein the first convexity is located at an apex of the section of the implant frame.

17. The subperiosteal dental implant according to claim 1, wherein the section of the implant frame further comprises first and second concavities formed at a junction of the first and second shoulders and the ridge.

18. The subperiosteal dental implant according to claim 1, further comprising at least one implant head extending from the implant frame.

19. The subperiosteal dental implant according to claim 1, wherein at least one intersecting strut extends between the first and second edges, the section of the implant frame corresponding to a section of the at least one intersecting strut.

20. The subperiosteal dental implant according to claim 1, wherein at least along the section, the cross-section profile defined by the gum-facing surface and the bone-facing surface only defines curved profiles.

21. A subperiosteal dental implant for receiving at least one replacement tooth of a patient, the subperiosteal dental implant comprising:
   an implant frame superposable to at least a section of a jaw bone of the patient, the implant frame having:
      a bone-facing surface at least partially contacting the jaw bone when the implant frame is superposed thereto, and
      a gum-facing surface, the gum-facing surface meeting the bone-facing surface at opposed first and second edges thereof, the gum-facing surface and the bone-facing surface being spaced-apart in-between the first and second edges, and along at least a section thereof, the implant frame comprising:
      a base defining at least partially the bone-facing surface and at least partially the gum-facing surface,
      a ridge protruding from the base and defining at least partially the gum-facing surface, the ridge being narrower than the base so as to define a first shoulder and a second shoulder between the ridge and each of the first and second edges.

* * * * *